US012472092B2

(12) United States Patent
Conti

(10) Patent No.: US 12,472,092 B2
(45) Date of Patent: *Nov. 18, 2025

(54) FLEXIBLE CONE-SHAPED INTRA-VAGINAL SUPPORT DEVICE

(71) Applicant: WATKINS-CONTI PRODUCTS, INC., Edmond, OK (US)

(72) Inventor: Allison Conti, Edmond, OK (US)

(73) Assignee: WATKINS-CONTI PRODUCTS, INC., Edmond, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,264

(22) Filed: Nov. 19, 2021

(65) Prior Publication Data

US 2022/0071800 A1 Mar. 10, 2022

Related U.S. Application Data

(63) Continuation of application No. 16/224,566, filed on Dec. 18, 2018, now Pat. No. 11,219,548, which is a (Continued)

(51) Int. Cl.
*A61F 6/12* (2006.01)

(52) U.S. Cl.
CPC ........ *A61F 6/12* (2013.01); *A61F 2230/0067* (2013.01)

(58) Field of Classification Search
CPC .... A61F 6/12; A61F 2230/0067; A61F 2/005; A61B 2017/00805; A61L 31/06
(Continued)

(56) References Cited

U.S. PATENT DOCUMENTS 1,996,242 A * 4/1935 Hagedorn ............. A61F 5/4553 604/330
2,089,113 A * 8/1937 Chalmers .............. A61F 5/4553 D24/141

(Continued)

FOREIGN PATENT DOCUMENTS

CN 102395336 A 3/2012
CN 209734284 U 12/2019

(Continued)

OTHER PUBLICATIONS

Office Action issued in Canadian Patent Application No. 2,996, 163 dated Sep. 23, 2022.

(Continued)

*Primary Examiner* — Sunita Reddy
(74) *Attorney, Agent, or Firm* — Michele V. Frank; Venable LLP

(57) ABSTRACT

In accordance with embodiments of the present disclosure, a flexible and non-absorbent vaginal insert device shaped to be held securely in place in a vagina when inserted, so as to improve symptoms associated with pelvic organ prolapse or urinary incontinence or both, is provided. The device is designed to be relatively easy to insert and remove. An applicator may be used to aid with insertion. The vaginal insert device comprises an upper portion, having a cone-shaped body, having a circular transverse cross-section throughout its length, having a wall with an interior side and an exterior side, an upper open end, a lower end, and a hollow interior, wherein the upper open end of the upper portion is the innermost portion of the device during insertion, and wherein the wall of the upper portion can be squeezed to make the upper portion more compact for easier insertion of the device, and wherein after insertion the wall expands back to its original shape. The device further comprises an exterior rim surrounding and protruding from
(Continued)

the exterior side of the wall and being adjacent to the upper open end, and a plurality of ridges surrounding and protruding from the exterior side of the wall, and a removal portion extending from said lower end of said upper portion to assist in removal of the device. The device can also comprise one or more ventilation openings.

16 Claims, 16 Drawing Sheets

Related U.S. Application Data continuation of application No. 15/242,105, filed on Aug. 19, 2016, now Pat. No. 10,188,545.

(60) Provisional application No. 62/283,092, filed on Aug. 20, 2015.

(58) Field of Classification Search
USPC .................................................... 600/29–32
See application file for complete search history.

(56) References Cited

U.S. PATENT DOCUMENTS 2,534,900 A * 12/1950 Chalmers .............. A61F 5/4553 604/330
2,613,670 A 10/1952 Sokolik
2,638,093 A 5/1953 Kulick
2,763,265 A 9/1956 Waters
3,404,682 A * 10/1968 Waldron ................. A61F 13/26 128/838
D222,013 S 9/1971 Thomas et al.
3,626,942 A 12/1971 Waldron
3,845,766 A * 11/1974 Zoller ................... A61F 5/4553 D24/141
D250,049 S 10/1978 Hite, Jr.
4,286,593 A 9/1981 Place et al.
4,825,686 A 5/1989 Marsh
D306,347 S 2/1990 Gyurik
D323,212 S 1/1992 Crawford
5,295,984 A * 3/1994 Contente ............... A61F 5/4553 604/327
5,782,745 A * 7/1998 Benderev ............... A61H 19/44 128/DIG. 25
5,813,973 A 9/1998 Gloth
5,827,248 A * 10/1998 Crawford .............. A61F 5/4553 604/328
D430,669 S 9/2000 Buck et al.
6,170,484 B1 1/2001 Feng
6,413,206 B2 7/2002 Biswas
6,503,190 B1 1/2003 Ulmsten et al.
6,558,370 B2 5/2003 Moser
6,733,438 B1 5/2004 Dann et al.
6,746,432 B2 6/2004 Zadini et al.
6,770,025 B2 8/2004 Zunker
6,773,421 B2 8/2004 Bosselaar et al.
7,577,476 B2 8/2009 Hochman et al.
7,771,344 B2 8/2010 Ziv
7,779,843 B2 8/2010 Astani et al.
7,892,163 B2 2/2011 Bartning et al.
D655,415 S 3/2012 Chaffringeon
D661,390 S 6/2012 McLain
D661,392 S 6/2012 McLain
8,302,608 B2 11/2012 Harmanli
8,652,026 B2 2/2014 Zunker
8,690,847 B2 4/2014 Norman
8,795,248 B2 8/2014 Shihata
D717,950 S 11/2014 Agrawal
D719,653 S 12/2014 Agrawal
8,911,344 B2 12/2014 Altan et al.
8,926,493 B2 1/2015 Karapasha
9,022,919 B2 5/2015 Ellefson et al.
D741,479 S 10/2015 Agrawal
D746,452 S 12/2015 Petrova
9,198,748 B2 12/2015 Ziv et al.
D760,897 S 7/2016 Teo
9,402,703 B2 8/2016 Ziv et al.
9,408,685 B2 8/2016 Hou et al.
D767,759 S 9/2016 Mcmillon-Nixon
9,555,168 B2 1/2017 Browning
9,918,702 B2 3/2018 Tariyal et al.
9,931,103 B1 4/2018 DeLaRosa
10,188,545 B2 1/2019 Conti
10,729,464 B1 8/2020 Booher, Sr.
11,000,402 B2 * 5/2021 Park ........................ A61F 5/448
11,337,788 B2 5/2022 Price et al.
11,446,011 B2 9/2022 Tariyal et al.
11,826,162 B2 11/2023 Sham
2002/0007106 A1 * 1/2002 Biswas ................... A61F 2/005 600/29
2003/0149334 A1 8/2003 Ulmsten et al.
2004/0054252 A1 * 3/2004 Zunker ................... A61F 2/005 600/29
2004/0249238 A1 12/2004 Farrell
2007/0203429 A1 8/2007 Ziv
2008/0077097 A1 3/2008 Chambers et al.
2008/0149109 A1 6/2008 Ziv
2009/0095304 A1 * 4/2009 Richardson ............. A61F 2/005 128/834
2009/0266367 A1 10/2009 Ziv et al.
2009/0283099 A1 11/2009 Harmanli
2010/0145137 A1 6/2010 Morgan
2010/0217068 A1 8/2010 Ziv et al.
2010/0312204 A1 12/2010 Sheu
2011/0065980 A1 3/2011 Ziv et al.
2011/0295058 A1 12/2011 Henriksson et al.
2012/0259167 A1 10/2012 Karapasha et al.
2013/0110060 A1 5/2013 Shihata
2013/0138134 A1 5/2013 Elman et al.
2014/0000628 A1 1/2014 Clark et al.
2014/0000629 A1 1/2014 Durling et al.
2014/0039245 A1 * 2/2014 Ziv ....................... A61F 2/0045 600/30
2014/0100416 A1 4/2014 Durling et al.
2014/0100417 A1 4/2014 Durling et al.
2015/0265456 A1 9/2015 Booher, Sr.
2016/0278988 A1 * 9/2016 Knox .................... A61F 15/005
2017/0049609 A1 2/2017 Conti
2017/0281325 A1 10/2017 Rosen et al.
2017/0360594 A1 12/2017 Park
2018/0028350 A1 2/2018 Wilson et al.
2018/0242957 A1 8/2018 Tariyal et al.
2018/0344300 A1 12/2018 Burrows et al.
2019/0117443 A1 4/2019 Conti
2019/0282350 A1 9/2019 Conti
2020/0078208 A1 3/2020 Stoebe-Latham
2022/0396836 A1 12/2022 Gire et al.
2023/0017064 A1 1/2023 Tariyal et al.
2023/0064804 A1 3/2023 Tariyal et al.

FOREIGN PATENT DOCUMENTS

DE 202009008893 U1 6/2009
DE 20 2017 106 300 U1 11/2017
EP 0504301 B1 3/2014
EP 3187156 A1 * 7/2017 ........... A61F 5/4553
ES 1064610 U 4/2007
GB 2364645 A 6/2002
IN 6032/CHE/2015 5/2017
JP 2010-515520 A 5/2010
JP 3177410 U 8/2012
KR 30-0707596 S 11/2013
KR 30-0914045 S 7/2017
KR 30-0914047 S 7/2017
KR 1020170120297 A 10/2017
KR 101961471 3/2019
KR 20190026534 A 3/2019
KR 102029068 B1 9/2019
KR 20190105743 A 9/2019
RU 94033073 A1 7/1996
RU 2272604 C2 3/2006

(56) References Cited

FOREIGN PATENT DOCUMENTS

| | | | | |
|---|---|---|---|---|
| RU | 2479284 | C2 | 4/2013 | |
| RU | 129391 | U1 | 6/2013 | |
| RU | 2570279 | C2 | 12/2015 | |
| TW | 200924721 | A | 6/2009 | |
| WO | 9843562 | A1 | 10/1998 | |
| WO | 2005087154 | A2 | 9/2005 | |
| WO | WO-2007082341 | A1 * | 7/2007 | ........... A61F 5/4553 |
| WO | 2011/013954 | A2 | 2/2011 | |
| WO | 2012/006670 | A1 | 1/2012 | |
| WO | 2013/108249 | A1 | 7/2013 | |
| WO | 2014/015975 | A1 | 1/2014 | |
| WO | 2015/041353 | A1 | 3/2015 | |
| WO | 2016025332 | A1 | 2/2016 | |
| WO | 2016149317 | A1 | 9/2016 | |
| WO | 2017/031456 | A1 | 2/2017 | |
| WO | 2017015767 | A1 | 2/2017 | |
| WO | 2017/161378 | A1 | 9/2017 | |
| WO | 2017180909 | A1 | 10/2017 | |
| WO | 2020/079677 | A1 | 4/2020 | |
| WO | 2021087374 | A1 | 5/2021 | |
| WO | 2021087395 | A1 | 5/2021 | |
| WO | 2022010891 | A1 | 1/2022 | |
| WO | 2022140447 | A1 | 6/2022 | |

OTHER PUBLICATIONS

Examination Report issued in Indian Patent Application No. 202017044574 dated Jul. 19, 2022.

Decision to Grant issued in Russian Patent Application No. 2020133900 dated Aug. 12, 2022.

Office Action issued in European Patent Application No. 19768216.4 dated Nov. 8, 2022.

Written Opinion and International Search Report mailed Nov. 17, 2016 in corresponding International Application No. PCT/US2016/047859 (9 pages).

Huang et al.; "Efficacy and Safety of Tension-Free Vaginal Tape-Secur Mini-Sling Versus Standard Midurethral Slings for Female Stress Urinary Incontinence: A Systematic Review and Meta-Analysis"; International Neurourology Journal, 2015, 19(4): pp. 246-258 (13 pages).

Ellington et al.; "Outcomes of Surgery for Stress Urinary Incontinence in the Older Woman"; Clin Geriatr Med., Nov. 2015, 31(4): pp. 487-505 (21 pages).

Jones et al.; "Pessary Use In Pelvic Organ Prolapse and Urinary Incontinence"; Reviews in Obstetrics & Gynecology, vol. 3, No. 1; pp. 3-9 (7 pages).

Petros et al.; An Integral Theory and Its Method for the Diagnosis and Management of Female Urinary Scandinavian Journal of Urology and Nephrology: Suppl No. 153: 1993; pp. 1-93 (93 pages).

Coelho et al: "Introduction of the method of intravaginal culture (IVC), through the device INVOCell routine laboratory RHA in Brazil"; JBRA Assisted Reproduction 2013; vol. 17 (No. 6): pp. 340-343 (4 pages); published Jan. 2013; doi: 10.5935/1518-0557.20130076.

Office Action from corresponding U.S. Appl. No. 15/242,105 dated May 17, 2018.

Office Action from corresponding U.S. Appl. No. 16/355,638 dated May 12, 2021.

Examination Report from corresponding Australian Application No. 2016308363 dated Jun. 15, 2020.

Notice of Allowance from corresponding U.S. Appl. No. 15/242,105 dated Nov. 16, 2018.

Notice of Acceptance from corresponding Australian Application No. 2016308363 dated Aug. 17, 2020.

Notice of Grant from corresponding Chinese Application No. 2016800486873 dated May 6, 2020.

Decision to Grant from corresponding Russian Application No. 218109509 dated Mar. 25, 2020.

Official Notification Prior to Acceptance from corresponding Israeli Application No. 257627 dated Apr. 29, 2021.

Decision to Grant from Japanese Application No. 2018-528215 dated Mar. 23, 2021.

International Search Report and Written Opinion from International Patent Application No. PCT/US2021/033732 dated Oct. 21, 2021.

Office Action from corresponding EP Application No. 16837928.7 dated Jun. 14, 2021.

First Examination Report mailed Feb. 1, 2021, in corresponding Indian Patent Application No. 201817007398 (5 pages).

Office Action issued in related Japanese Patent Application No. 2018-528215 dated Jul. 27, 2020.

Office Action issued in related Russian Patent Application No. 2018109509 dated Dec. 5, 2019.

Search Report issued in related Russian Patent Application No. 2018109509 dated Dec. 5, 2019.

Office Action issued in related Chinese Patent Application No. 2016800486873 dated Aug. 27, 2019.

Extended European Search Report issued in counterpart European Patent Application No. 16837928.7 dated May 7, 2019.

International Search Report and Written Opinion issued in counterpart International Patent Application No. PCT/US2019/022624 dated Jun. 11, 2019.

Customer Review of Collapsible Silicone Cup for Sterilizing Your Diva Cup and Storing Menstrual Cups-Foldable for Travel (Amazon.com) Jan. 17, 2018, https://Www.amazon.com/review/RJ84O5XNN0ZY9/ref=cm_cr_srp_d_rdp_permie=UTF8&ASIN=B074PBX6ZY.

Nurse Hatty Kegel Exercise Weight System (Amazon.com) 2016 https://amazon/com/Nurse-Hatty-Exercise-Weight-System/dp/B01FQ21X16/ref=cm_cr_srp_d_product_top?ie=UTF8&th=1.

Shanna Atnip et al., "Vaginal Support Pessairies: Indications for Use and Fitting Strategies" Urologic Nursing, vol. 32, p. 121, table 4, steps 8-9, May-Jun. 2012.

Inomata Japanese Rice Washing Bowl with Side and Bottom Drainers, Clear (Amazon.com) 2016, http://www.amazon.com/Inomata-Japanese-Washington-Bottom-Drainers/dp/B004QZAAS2.

Office Action from corresponding U.S. Appl. No. 16/355,638 dated Mar. 12, 2021.

Notice of Allowance from corresponding U.S. Appl. No. 16/355,638 dated Oct. 22, 2021.

Office Action from corresponding U.S. Appl. No. 16/224,566 dated Oct. 7, 2020.

Office Action from corresponding U.S. Appl. No. 16/224,566 dated Feb. 19, 2021.

Notice of Allowance from corresponding U.S. Appl. No. 16/224,566 dated Nov. 5, 2021.

Office Action issued in related Russian Patent Application No. 2020133900 dated Dec. 9, 2021.

Search Report issued in related Russian Patent Application No. 2020133900 dated Dec. 6, 2021.

First Office Action from Chinese Application No. 201980019605.6 dated Jan. 31, 2023.

Patent Examination Report from New Zealand Application No. 740253 dated Feb. 9, 2023.

European Search Report from European Patent Application No. 19768216.4 dated Nov. 24, 2021, 8 pages.

First Office Action from Taiwanese Patent Application No. 108109125 dated Mar. 27, 2023.

Office Action from Mexican Application No. MX/a2018/002175 dated Apr. 13, 2023.

Notification of Reasons for Rejections from Japanese Patent Application No. 2020-573093 dated Apr. 24, 2023.

Notice of Preliminary Rejection from Korean Patent Application No. 10-2018-7007430 dated May 2, 2023.

Notice of Allowance from Canadian Application No. 2,996,163 dated Jun. 20, 2023.

Office Action from Brazilian Patent Application No. BR112020018830-1 dated Apr. 6, 2023.

Office Action from Israel Patent Application No. 277232 dated Jun. 29, 2023.

Hearing Notice from Indian Patent Application No. 201817007398 dated Apr. 18, 2023.

(56) References Cited

OTHER PUBLICATIONS

Communication under Rule 71(3) EPC from European Application No. 16837928.7 dated May 9, 2023.
Notice of Allowance from Mexican Application No. MX/a2018/002175 dated Jul. 18, 2023.
Patent Examination Report 2 from New Zealand Patent Application No. 740253 dated Aug. 16, 2023, 3 pages.
Notice of Acceptance from New Zealand Patent Application No. 7402532 dated Dec. 5, 2023, 2 pages.
Notification of Second Office Action from Chinese Patent Application No. 201980019605.6 dated Sep. 29, 2023, 14 pages.
Notification of Reason for Rejection from Japanese Patent Application No. 2020-573093 dated Nov. 1, 2023, 13 pages.
Non-Final Office Action from U.S. Appl. No. 17/555,098 dated Dec. 22, 2023, 11 pages.
Notice of Preliminary Rejection from Korean Patent Application No. 10-2020-7029289 dated Dec. 8, 2023, 14 pages.
Office Action from Canadian Patent Application No. 3,091,965 dated Oct. 31, 2023, 12 pages.
Communication under Rule 71(3) EPC from European Patent Application No. 19768216.4 dated Dec. 1, 2023, 7 pages.
Allowance Decision of Examination from Taiwan Patent Application No. 108109125 dated Dec. 18, 2023, 3 pages.
Examination Report No. 1 from Australian Patent Application No. 2019233913 dated Dec. 6, 2023, 4 pages.
Notice of Last Preliminary Rejection from Korean Patent Application No. 10-2018-7007430 dated Nov. 10, 2023, 4 pages.
Hearing Notice from Indian Patent Application No. 201817007398 dated Jul. 12, 2023, 2 pages.
Extended European Search Report from European Patent Application No. 21807880.6 dated Apr. 24, 2024, 11 pages.
Notice of Allowance from U.S. Appl. No. 17/555,098 dated May 15, 2024, 10 pages.
Notice of Allowance from Mexican Patent Application No. MX/a/2020/009620 dated Jun. 24, 2024.
Notice of Allowance from Korean Patent Application No. 10-2018-7007430 dated Jun. 25, 2024.
Office Action from Mexican Patent Application No. MX/a/2020/009620 dated Feb. 6, 2024.
Notification to Grant Patent from Chinese Patent Application No. 201980019605.6 dated Feb. 26, 2024.
Decision to Grant a Patent from Japanese Patent Application No. 202-573093 dated Apr. 2, 2024.
Examination Report No. 2 from Australian Patent Application No. 2019233913 dated Mar. 28, 2024.
Office Action from Israeli Patent Application No. 277232 dated Jun. 3, 2024.
Extended European Search Report from EP Patent Application No. 24175756.6 dated Jul. 30, 2024.
Office Action from JP Patent Application No. 2023-119948 dated Aug. 6, 2024.
Office Action from KR Patent Application No. 10-2020-7029289 dated Aug. 29, 2024.
Office Action from TW Patent Application No. 113110084 dated Sep. 2, 2024.
Office Action from Brazil Patent Application No. 112020018830-1 mailed Oct. 2, 2024.
Amazon1: May 9, 2018 Collapsible Silicone Cup for Sterilizing and Storing Your Diva Cup https://www.amazon.com/Collapsible-Silicone-Foldable-Sterilizing-Menstrual/product-reviews/B07DCBTY1H/ref=cm_cr_getr_d_paging_btm_next_6? ie=UTF8&reviewerType=all_reviews&pageNumber=6.
Amazon2: Jul. 8, 2016 Nurse Hatty Kegel Exercise Weight System https://www.amazon.com/Nurse-Hatty-Exercise-Weight-System/dp/B01FQ21X16/ref=cm_cr_srp_d_product_top?ie=UTF8&th=1.
Office Action from CA Application No. 3,091,965 dated Oct. 18, 2024, 7 pages.
Notice of Allowance directed to Korean Patent Application No. 10-2020-7029289 dated Nov. 27, 2024, 5 pages.
Decision of Grant directed to Japanese Patent Application No. 2023-119948 dated Dec. 12, 2024, 2 pages.
Allowance Decision of Examination directed to Taiwan Patent Application No. 113110084 dated Feb. 8, 2025, 3 pages.
Office Action directed to Israeli Patent Application No. 298398 dated Dec. 31, 2024, 4 pages.
Office Action directed to Chinese Patent Application No. 202180046208.5 dated Jan. 15, 2025, 17 pages.
Office Action directed to Russian Patent Application No. 2022133419 dated Mar. 7, 2025, 11 pages.
Office Action directed to Japanese Patent Application No. 2024-088083 dated May 7, 2025, 6 pages.
Office Action directed to Japanese Patent Application No. 2022-571302 dated Jul. 15, 2025, 7 pages.
Notification of Second Office Action to Chinese Patent Application No. 202180046208.5 dated Aug. 4, 2025, 20 pages.
Notice of Preliminary Rejection directed to Korean Patent Application No. 10-2022-7044190 dated Jul. 9, 2025, 11 pages.
Communication pursuant to Article 94(3) EPC directed to EP Patent Application No. 21807880.6 dated Aug. 18, 2025, 6 pages.
Office Action directed to TW Patent Application No. 114117559 dated Oct. 9, 2025, 5 pages.
Search Report directed to TW Patent Application No. 114117559 dated Oct. 5, 2025, 1 page.
Office Action directed to RU Patent Application No. 2022133419/14 dated Sep. 5, 2025, 9 pages.

* cited by examiner

FIG. 4
28
BACKPASSAGE
PROLAPSE/RECTOCCLE

SECTION A-A

FLEXIBLE CONE-SHAPED INTRA-VAGINAL SUPPORT DEVICE

CROSS-REFERENCE TO RELATED APPLICATIONS

This application is a continuation of U.S. application Ser. No. 16/224,566, filed Dec. 18, 2018, which claims priority to U.S. application Ser. No. 15/242,105, filed Aug. 19, 2016, now U.S. Pat. No. 10,188,545, which claims priority to U.S. Provisional Application No. 62/283,092, filed Aug. 20, 2015, the contents of all of which are hereby incorporated by reference in their entireties.

TECHNICAL FIELD

The present disclosure relates in general to a flexible and non-absorbent vaginal insert device for use in improving symptoms associated with pelvic organ prolapse and urinary incontinence when the device is inserted, and more particularly to a vaginal insert device that is easier to insert and remove.

BACKGROUND

Stress Urinary Incontinence (SUI) and Pelvic Organ Prolapse (POP) are growing problems globally that not only cost health care systems large amounts of money, but severely degrade the quality of life of tens of millions of women in the United States alone. Although surgical solutions can succeed in ameliorating symptoms associated with SUI and POP, surgery is not without risks and complications and may even leave the patient in a worse situation than before treatment. See Huang W, Wang T, Zong H, Zhang Y, *Efficacy and Safety of Tension-Free Vaginal Tape-Secure Mini-Sling Versus Standard Midurethral Slings for Female Stress Urinary Incontinence: A Systematic Review and Meta-Analysis*, International Neurourology Journal, 2015, 19 (4): 246-58, which is incorporated herein by reference. See also Ellington D R, Erekson E A, Richter H E, *Outcomes of Surgery for Stress Urinary Incontinence in the Older Woman*, Clin Geriatr Med., 2015, 31 (4): 487-505, which is incorporated herein by reference. The FDA has issued several Public Health Notifications regarding surgical mesh placed through the vagina (transvaginal placement) to treat POP and SUI. The FDA identified serious and frequent complications with surgical mesh, including mesh erosion through the vagina, pain, infection, bleeding, discomfort during intercourse, organ perforation, urinary problems, recurrent prolapse, neuro-muscular problems, vaginal scarring/shrinkage & emotional problems. Most surgical complications require intervention including medical, additional surgical treatment and hospitalization.

Prior art pessaries, which have been most commonly used for management of female POP but also have been used for SUI, have presented a viable non-surgical option for treating SUI and POP. These prior art pessaries have had few complications and side effects. However, these devices are traditionally placed in the vagina for an extended period of time. They may also be uncomfortable. Furthermore, these prior art devices have been difficult for the patient to insert and remove, and use, insertion and removal of these devices have often required regular office visits with a physician for years. See, Jones K A, Harmanli O, *Pessary Use in Pelvic Organ Prolapse and Urinary Incontinence*, Rev Obstet Gynecol, 2010, 3 (1): 3-9, which is incorporated herein by reference. Difficulty with self-removal and insertion of the pessary, having the pessary fall out during defecation, and lack of comfort and convenience may be limiting widespread use of the prior art devices.

Stress Urinary Incontinence (SUI) in women, is the involuntary leakage of urine due to a weakened pelvic support system and/or pressure on the bladder from aging, genetics, or childbirth. The Urology Care Foundation estimates that one of every three women will experience SUI at some point in their lifetime. There are a few types of urinary incontinence including stress incontinence, urge incontinence and mixed incontinence. All are mainly due to connective tissue laxity or damage in the vagina or supportive ligaments. See *An Integral Theory and Its Method for the Diagnosis and Management of Female Urinary Incontinence*, Petros P E, Ulmsten U I, Scand J Urol Nephrol Suppl, 1993, 153, 1-93, which is incorporated by reference. FIG. 1 is a cross-section of the pelvic region of a female with normal anatomy illustrating the uterus 10, cervix 12, bladder 14, urethra 16, vagina 18, and rectum 20. FIG. 2 illustrates urinary incontinence (i.e., leakage of urine) 22 caused by stress or pressure 24 on the bladder 14. Involuntary leakage of urine often occurs during activities such as coughing, laughing, sneezing, lifting or exercise.

Connective tissue damage to three zones of the Integral System, which encompasses all three pelvic organs, including the bladder, vagina and ano-rectum, is the ultimate cause of Pelvic Organ Prolapse (POP) and dysfunction in these organs. FIG. 3 is a cross-section of the pelvic region of a female with a prolapsed bladder 26. FIG. 4 is a cross-section of the pelvic region of a female with a prolapsed back-passage 28. FIG. 5 is a cross-section of the pelvic region of a female with a prolapsed uterus 30. POP is commonly due to child bearing but may also be caused simply by genetics and the aging process.

Therefore, there is a need for a pessary or other vaginal insert device that manages, improves, or eliminates female incontinence, POP or both incontinence and POP. There is a further need for such a pessary or other vaginal insert device that does not require a prescription, and is non-absorbent, over the counter, convenient, comfortable, and easy for a patient to insert and remove, with no or minimal physician intervention. Preferably such a vaginal insert device would also be reusable, but it also can be disposable.

SUMMARY

In accordance with the teachings of the present disclosure, the disadvantages and problems associated with prior art pessaries may be substantially reduced or eliminated.

In accordance with embodiments of the present disclosure, a vaginal insert device for use in improving symptoms associated with pelvic organ prolapse, urinary incontinence, or both pelvic organ prolapse and urinary incontinence can include an upper portion, which is made of an elastic and non-absorbent material, having a cone-shaped body, having a circular transverse cross-section throughout its length, having a wall with an interior side and an exterior side, an upper open end, a lower end, and a hollow interior, wherein the circumference of the upper portion decreases from the upper open end to the lower end, wherein the upper open end of the upper portion is the innermost portion of the vaginal insert device during insertion, and wherein the wall of the upper portion can be squeezed to make the upper portion more compact for easier insertion of the vaginal insert device, and wherein the wall expands back to its original shape after insertion. Such vaginal insert device can further include: an exterior rim surrounding and protruding from the exterior side of the wall of the upper portion and being adjacent to the upper open end; and a plurality of ridges surrounding and protruding from the exterior side of the wall of the upper portion and being spaced apart from the upper open end to the lower end.

In accordance with these and other embodiments of the present disclosure, a vaginal insert device can include a removal portion extending from the lower end of the upper portion, wherein the removal portion can be accessed from the exterior of a vagina when the vaginal insert device is inserted in the vagina, and wherein the removal portion assists in removal of the vaginal insert device from the vagina. The removal portion can comprise a string or a stem. In the embodiment where the removal portion is a stem, the stem can extend from the lower end of the upper portion, wherein the upper portion and the stem comprise an integral one-piece device made from the elastic and non-absorbent material, wherein the stem has a cone-shaped body, having a circular transverse cross-section throughout its length, having a wall, an upper end, a lower open end, and a hollow interior, and wherein the circumference of the stem increases from the upper end to the lower open end. The removal portion can also have a plurality of ridges like the upper portion.

In accordance with these and other embodiments of the present disclosure, a vaginal insert device can include one or more ventilation openings. A ventilation hole can be located at the point where the lower end of the upper portion and a stem intersect. One or more ventilation openings can also be located in the wall on the upper portion.

In accordance with these and other embodiments of the present disclosure, a vaginal insert device can include an exterior rim which is circular and has a first section and a second section, wherein the first section protrudes from the exterior side of the wall of the upper portion a greater distance than the second section.

In accordance with these and other embodiments of the present disclosure, a vaginal insert device can include an applicator used during insertion of the device, wherein the applicator can contain at least the upper portion when it is in a more compact shape, and wherein the applicator assists in the insertion of the device.

Medical and other advantages of the present disclosure may be readily apparent to one skilled in the art from the figures, description and claims included herein. The objects and advantages of the embodiments will be realized and achieved at least by the elements, features, and combinations particularly pointed out in the claims.

It is to be understood that both the foregoing general description and the following detailed description are examples and explanatory and are not restrictive on the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Preferred embodiments and their advantages are best understood by reference to FIGS. 6A through 15C, wherein like numbers are used to indicate like and corresponding parts or sections.

The vaginal insert device of the present invention manages, improves, or eliminates female urinary incontinence, Pelvic Organ Prolapse (POP), or both POP and urinary incontinence. It does not require a prescription, and is non-implantable, non-absorbent, over the counter, convenient, flexible, comfortable, and easy for a patient to insert and remove, with no or minimal physician intervention. Preferably such a vaginal insert device would also be reusable, but it also can be disposable. It eliminates concern of Toxic Shock Syndrome (TSS) by not consisting of an absorbency element which could produce odor and breed bacteria. The device of the present invention is fabricated, such as by a molding process, with an elastic and non-absorbent material, preferably a biocompatible elastomer such as medical grade silicone. An example of a silicone material suitable for use in the present invention is NuSil Technology's MED-4950 product, which is characterized as a liquid silicone rubber.

The vaginal insert device of the present invention is shaped so that it is held securely in place in the vagina when inserted, as well as shaped to impose pressure on the urethral sphincter and to support pelvic organs. One exemplary use of the vaginal insert device of the present invention is for management of stress urinary incontinence (SUI) and the involuntary leakage of urine during activities such as coughing, laughing, sneezing, lifting and exercise for patients over the age of eighteen. It is expected that the device will typically be inserted by an adult woman for up to about twelve hours or more, depending on their comfort level.

Figure 1:
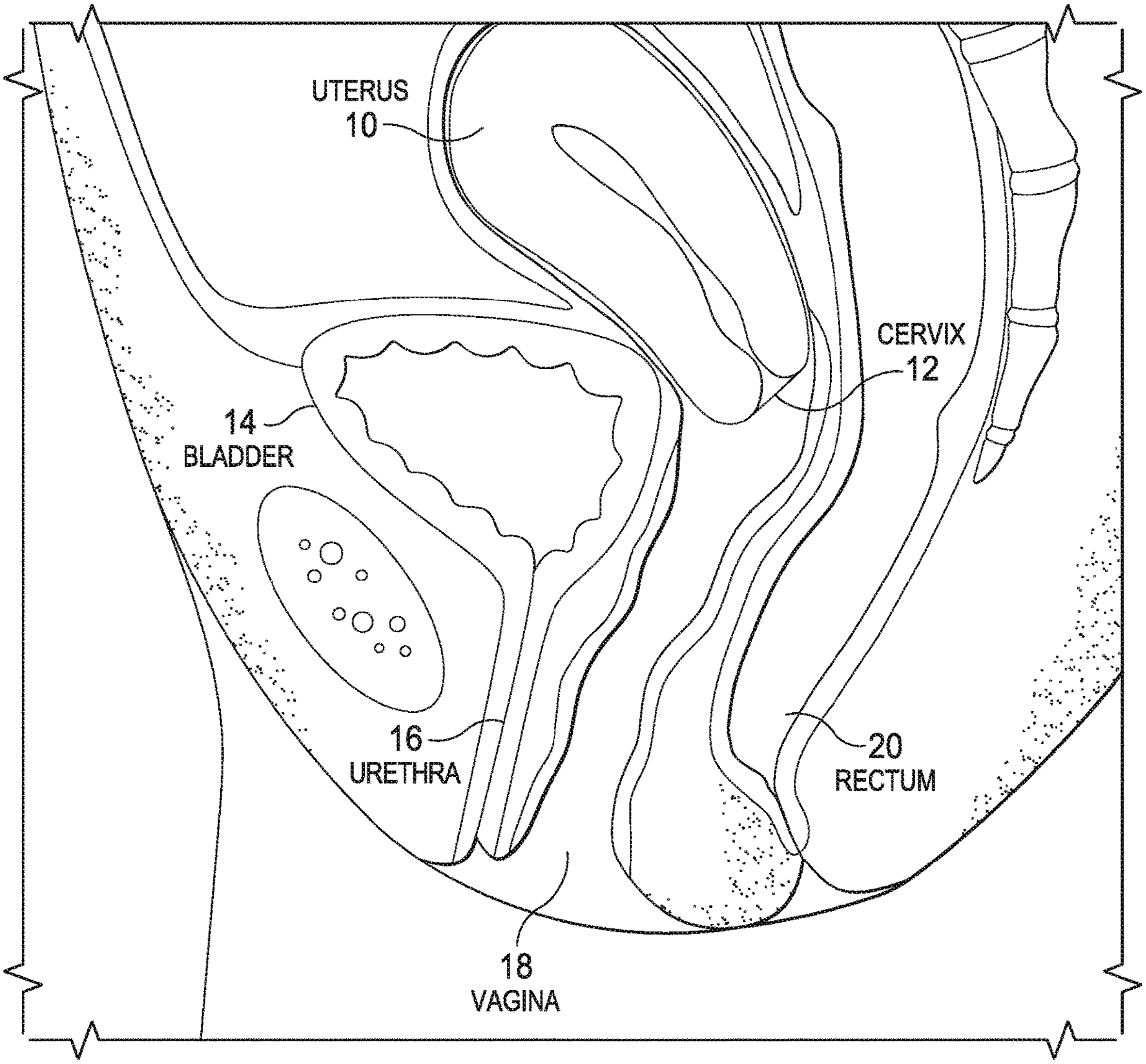
FIGS. 1-5 each illustrate a cross-section of the pelvic region of a female for purposes of discussing the background of the present disclosure.
Figure 2:
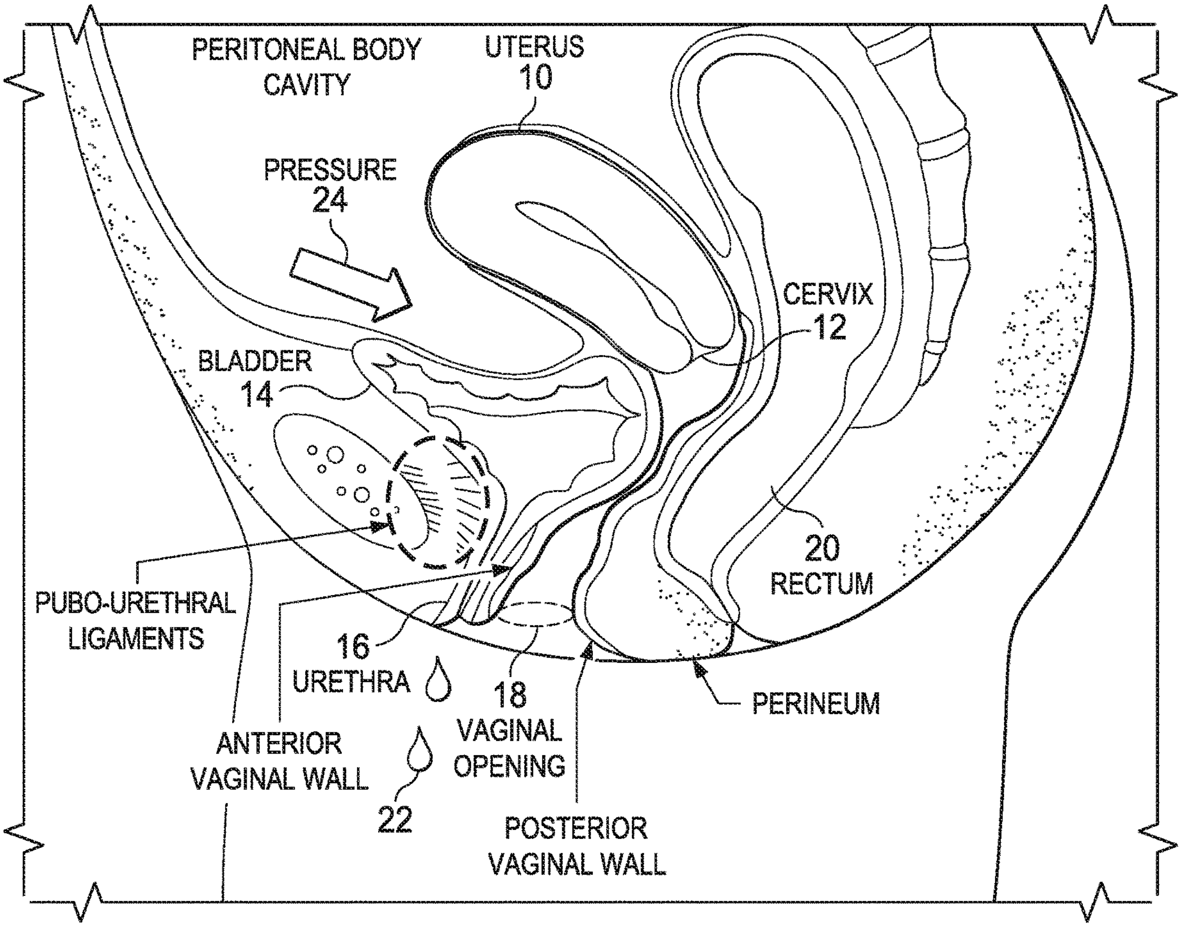
Figure 3:
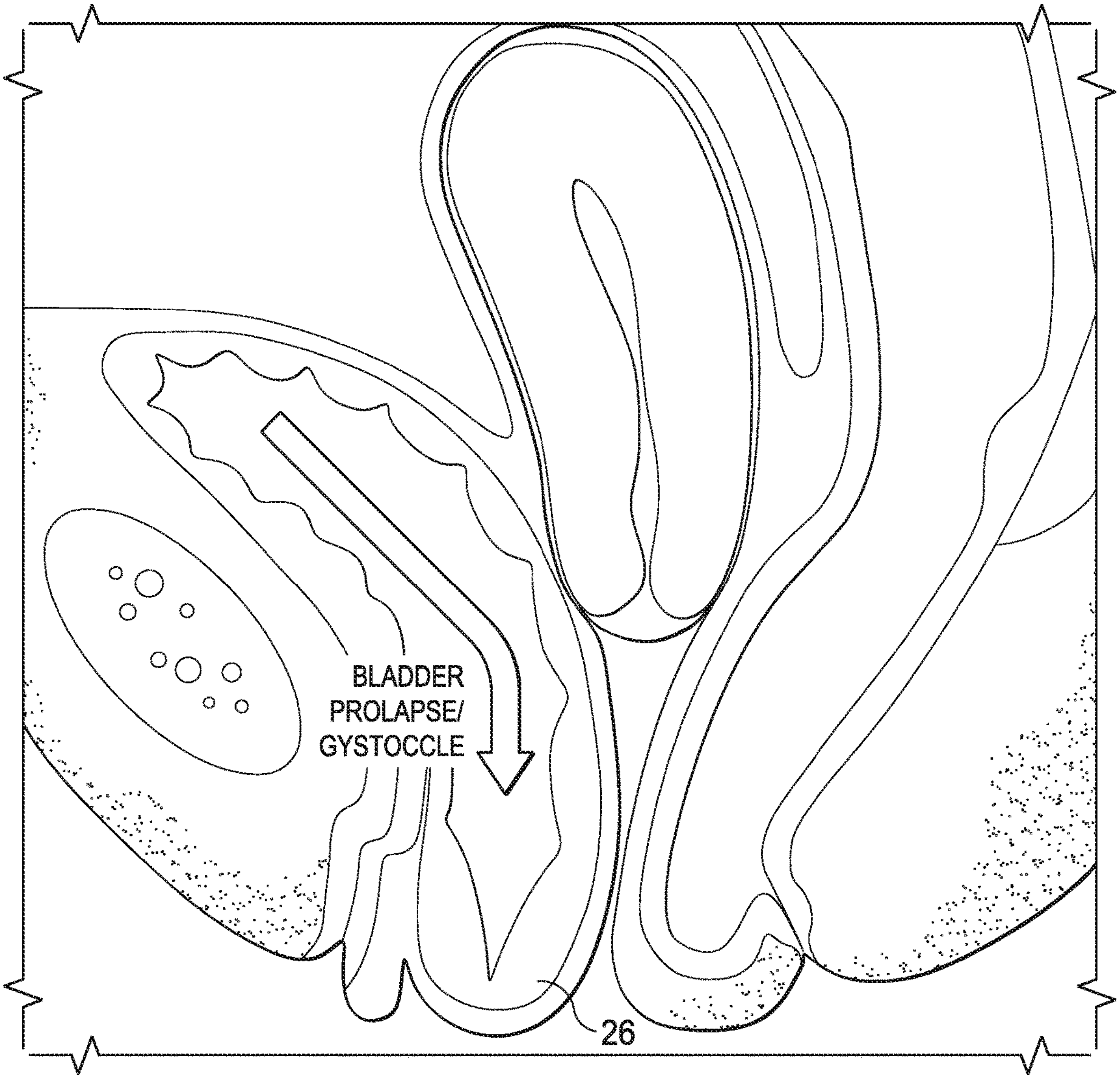
Figure 4:
Figure 5:
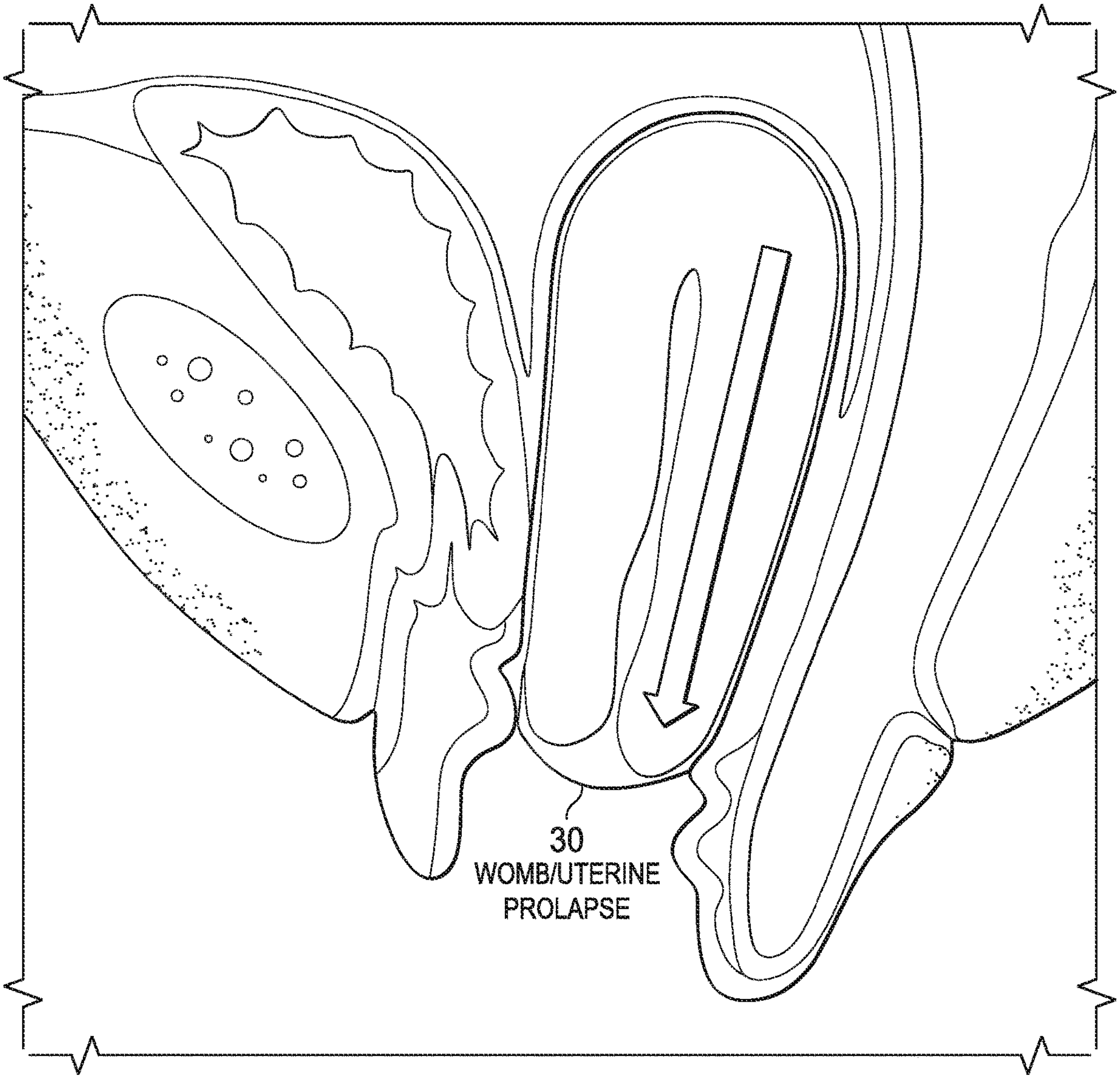
Figure 6A:
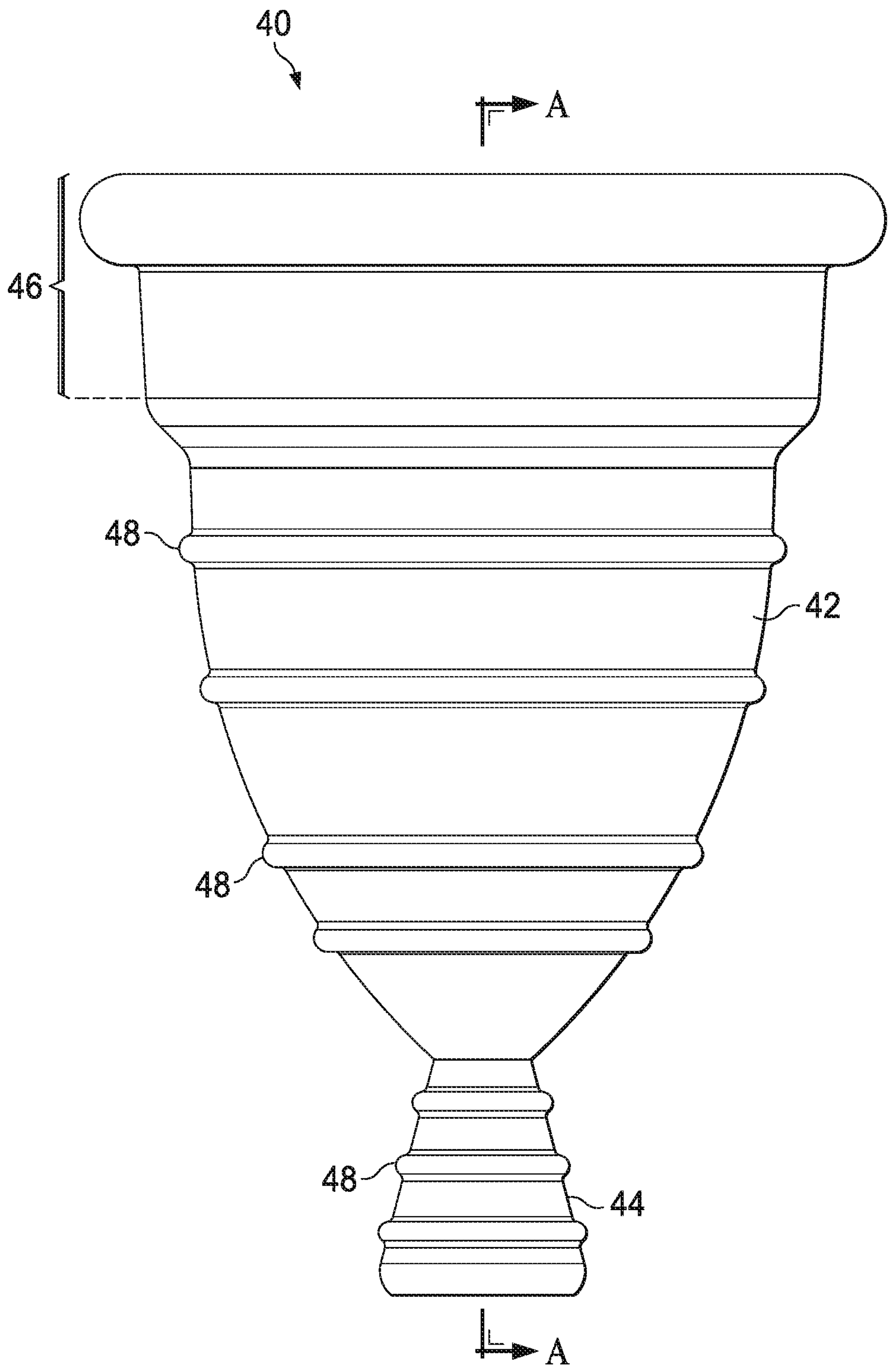
FIG. 6A illustrates a side view of an example vaginal insert device, in accordance with embodiments of the present disclosure.

FIG. 6A illustrates a side view of an example vaginal insert device 40, in accordance with embodiments of the present disclosure. The vaginal insert device 40 of FIG. 6A comprises an upper portion 42 and a lower, stem-like, removal portion 44. As further illustrated and described in more detail below, the upper portion 42 includes a rim 46 as well as ridges 48 which are preferably spaced apart from the top of the upper portion to the lower end of the upper portion. Ridges 48 can be randomly or uniformly spaced. The removal portion can also have ridges 48, which like the upper portion are spaced apart from the top of the removal portion to the lower end of the removal portion.

Figure 6B:
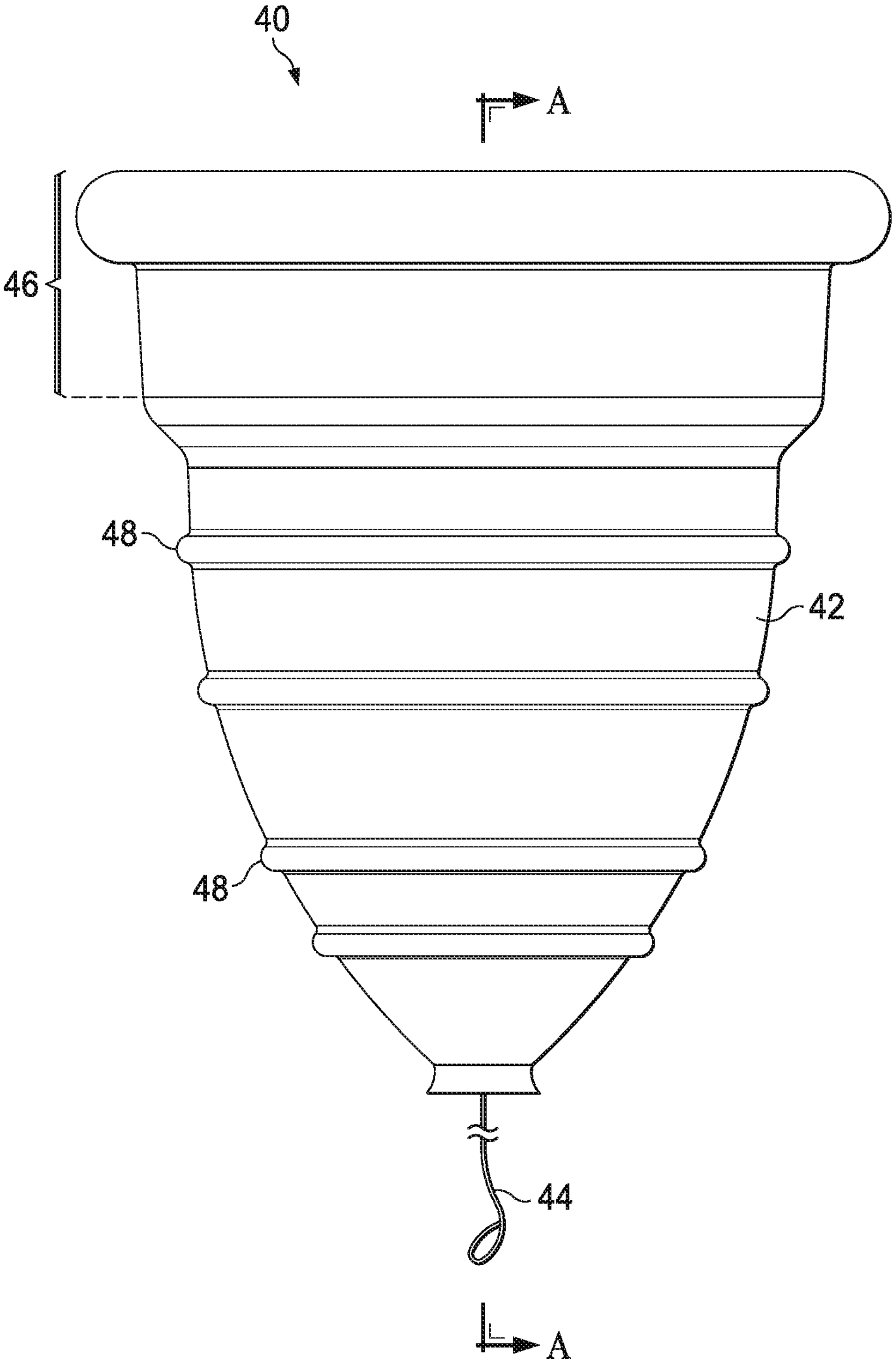
FIG. 6B illustrates a side view of another example vaginal insert device, in accordance with embodiments of the present disclosure.

FIG. 6B illustrates a side view of another example vaginal insert device 40, in accordance with embodiments of the present disclosure. In this embodiment, device 40 is the same as the embodiment shown in FIG. 6A except the removal portion 44 is a string, cord or ribbon (collectively referred to as "a string"), such as is used in removing a tampon.

Figure 7:
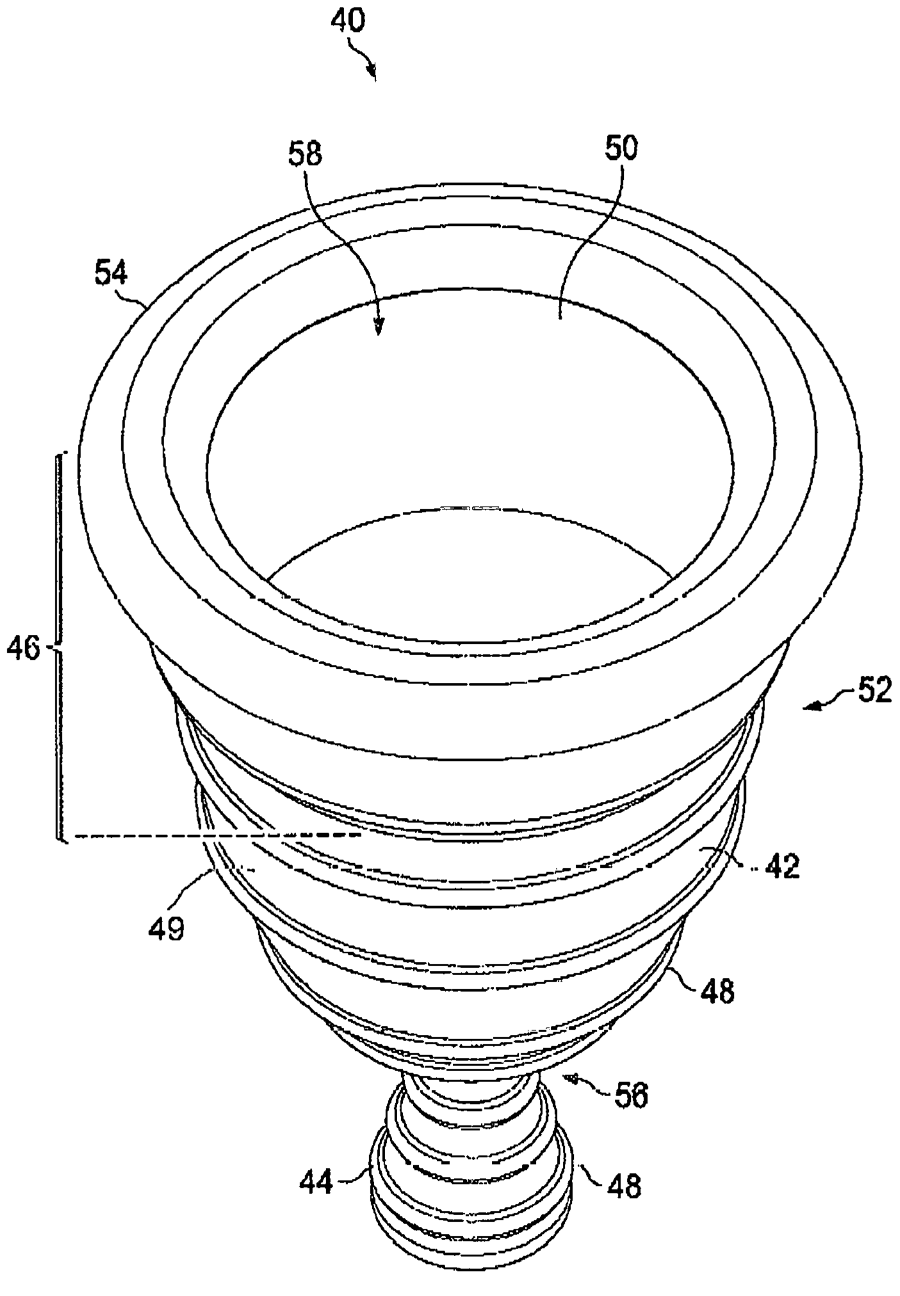
FIG. 7 illustrates a perspective view of the vaginal insert device of FIG. 6A.

FIG. 7 illustrates a perspective view of the vaginal insert device 40 of FIG. 6A. As shown in FIG. 7, the upper portion 42 has a cone-shaped body, having a circular transverse cross-section throughout its length, has a wall 49 with an interior side 50 and an exterior side 52, an upper open end 54, a lower end 56, and a hollow interior 58, wherein the circumference of the upper portion decreases from the upper open end to the lower end. As illustrated, rim 46 is preferably circular and surrounds and protrudes from the exterior side 52 of the wall and is adjacent to the upper open end 54. Ridges 48 are preferably circular rings which surround the exterior side 52 of wall 49. As further illustrated, a stem or removal portion 44 extends from the lower end 56 of the upper portion 42. The upper portion 42 and the stem 44 can be fabricated as an integral one-piece device. FIG. 7 also illustrates that the stem 44 can have a cone-shaped body.

Figure 8:
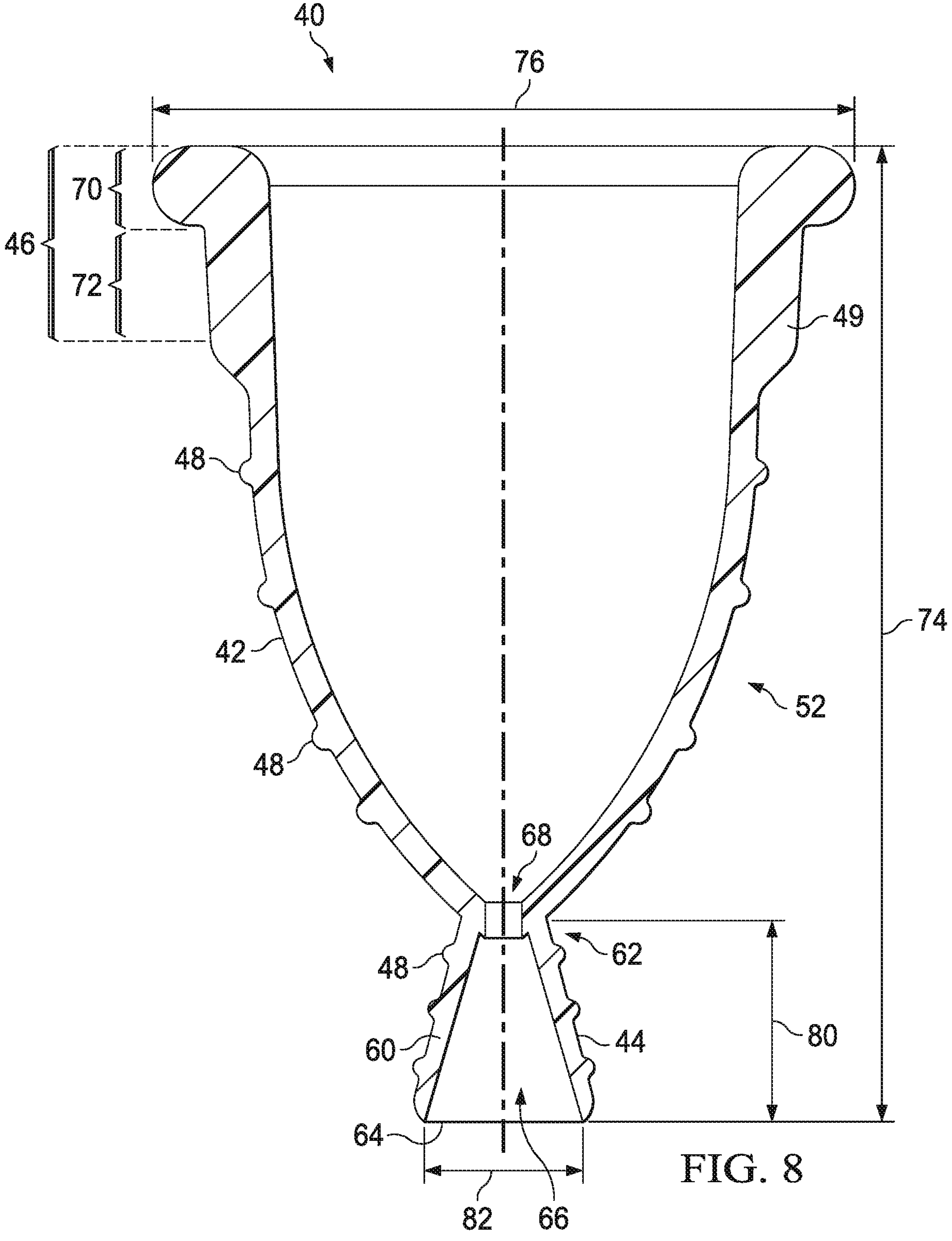
FIG. 8 is a cross-sectional view of vaginal insert device of FIG. 6A across section line A-A.

FIG. 8 is a cross-sectional view of vaginal insert device 40 of FIG. 6A across section line A-A. As shown in FIG. 8, stem 44 can have a circular transverse cross-section throughout its length, having a wall 60, an upper end 62, a lower open end 64, and a hollow interior 66, wherein the circumference of the stem increases from the upper end to the lower open end. As illustrated, ridges 48 protrude from the exterior side 52 of the wall 49.

FIG. 8 further illustrates an embodiment of vaginal insert device 40 which includes a ventilation opening 68. The ventilation opening can include a ventilation hole, a screen or a mesh or any other component with an opening. As would be understand by one of ordinary skill of the art, vaginal insert device 40 can include a plurality of ventilation openings in locations other than, or in addition to, ventilation opening 68, such as in wall 49 of the upper portion 42. The one or more ventilation openings are intended to make the vaginal insert device more comfortable for the patient when inserted. The one or more openings may also equalize the air pressure between the inside and outside of the vagina 18, when vaginal insert device 40 is inserted. However, having a ventilation opening is not required for the vaginal insert device to be comfortable, useful and effective.

FIG. 8 illustrates further detail regarding an embodiment where rim 46 has a first section 70 and a second section 72, both of which protrude from the exterior side 52 of the wall 49, with the first section protruding a greater distance than the second section. A person of ordinary skill in the art would understand that multiple alternative embodiments of rim 46 are possible, including an embodiment in which rim 46 comprises just the first section 70, or another embodiment in which rim 46 comprises only one section but has a greater height than first section 70 and protrudes from the exterior side 52 of the wall the same distance from the top of the rim to the bottom of the rim. In another embodiment, rim 46 surrounds the exterior side 52 of the wall 49, adjacent to the upper open end 54, and comprises sections which protrude and sections which do not protrude from the exterior side of the wall.

With reference to FIGS. 7 and 8, the term "ridges" is intended to be broadly defined. Accordingly, ridges 48 can include the embodiment illustrated in FIGS. 7 and 8, in which ridges 48 are protrusions which are preferably circular rings which surround the exterior side of wall 49. However, "ridges" can also include any protrusions that extend from the exterior side 52 of wall 49, such as a plurality of studs or knobs.

A person of ordinary skill in the art would understand that the vaginal insert device 40 can come in different sizes, including different sizes to accommodate adult women with differing anatomy. Furthermore, a person of ordinary skill in the art would understand that the dimensions of the various sections and portions of the device 40 can be modified from the multiple embodiments illustrated and disclosed herein. For example, referring to FIG. 8, the total height 74 of device 40, diameter 76 at the upper open end 54 of the upper portion 42, and thickness of the wall 49 of the upper portion 42 of the device 40 can be modified, while retaining or improving on the intended usefulness, effectiveness and other benefits of the device. The following non-exclusive list of dimensions, in reference to FIG. 8, are non-limiting examples of embodiments of device 40 which are believed to be suitable for most women, and which provide the intended usefulness, effectiveness and other benefits of the device. For example, a suitable total height of device 40 is estimated to be in the range of about 58.0 to 67.0 millimeters (mm), and a suitable outer diameter 76 is estimated to be in the range of about 38.0 to 44.0 mm. A suitable height of the stem 44 is estimated to be in about the 13.0 to 15.0 mm range. A suitable thickness of the wall 49, in sections without ridges 48, of the upper portion 42, below rim 46, is estimated to be about 2.0 mm, whereas a suitable thickness of the wall 49, in sections with ridges is estimated to be about 2.5 mm. Wall 60 of stem 44 is estimated to have a suitable thickness of about 1.25 mm in sections without ridges 48. A suitable height of rim 46 is estimated to be about 15.0 mm, with a suitable height of first section 70 estimated to be about 5.0 mm and a suitable height of second section 72 estimated to be about 10.0 mm. A suitable thickness of the first section 70 is estimated to be about 6.0 mm and the second section 72 is estimated to be about 4.0 mm. A suitable outer diameter 82 of lower open end 64 is estimated to be about 10.5 mm. A suitable diameter of ventilation opening 68 is estimated to be about 2.0 mm.

Figure 9:
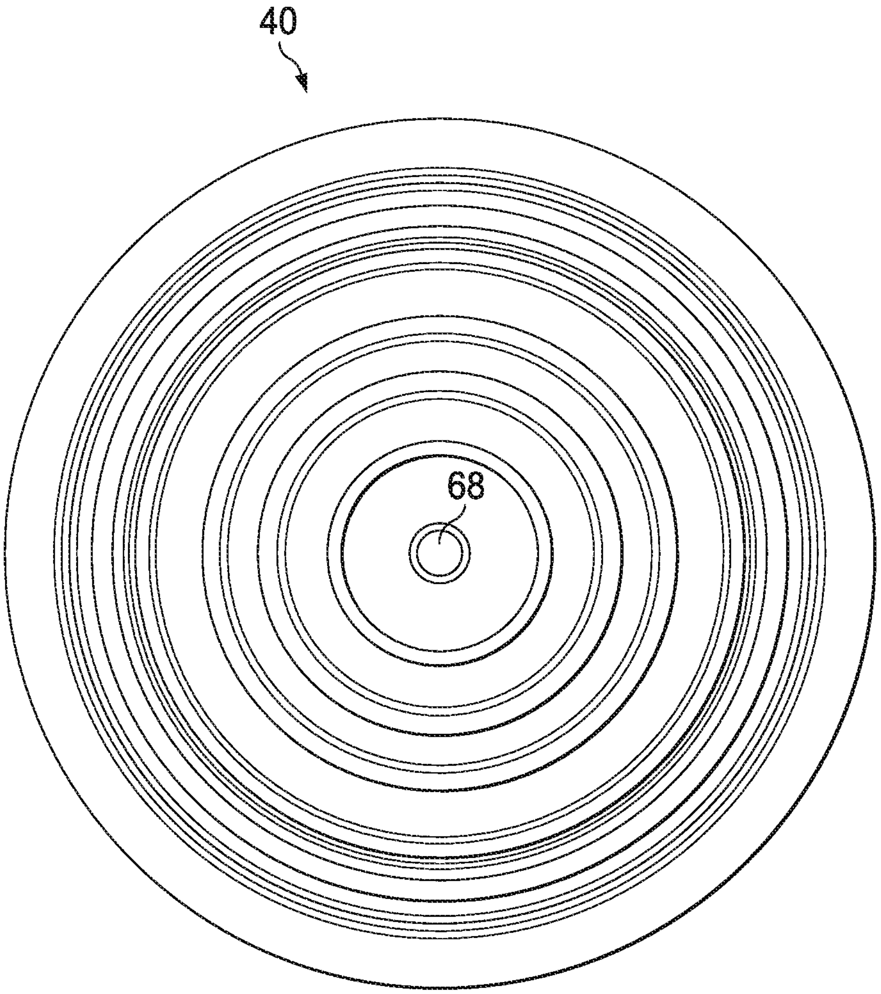
FIG. 9 is a bottom view of the vaginal insert device of FIG. 6A.
Figure 10:
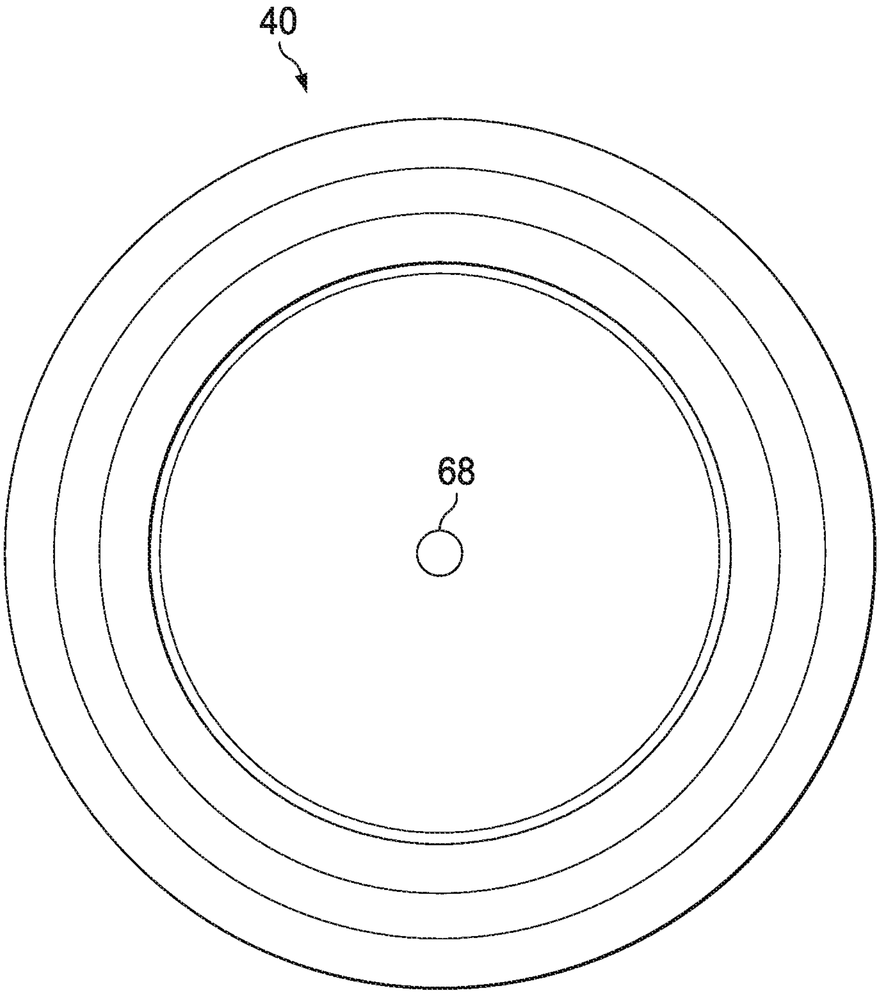
FIG. 10 is a top view of the vaginal insert device of FIG. 6A.

FIG. 9 is a bottom view of the vaginal insert device 40 of FIG. 6A for an embodiment having ventilation opening 68. FIG. 10 is a top view of the vaginal insert device 40 of FIG. 6A for an embodiment having ventilation opening 68.

Figure 11:
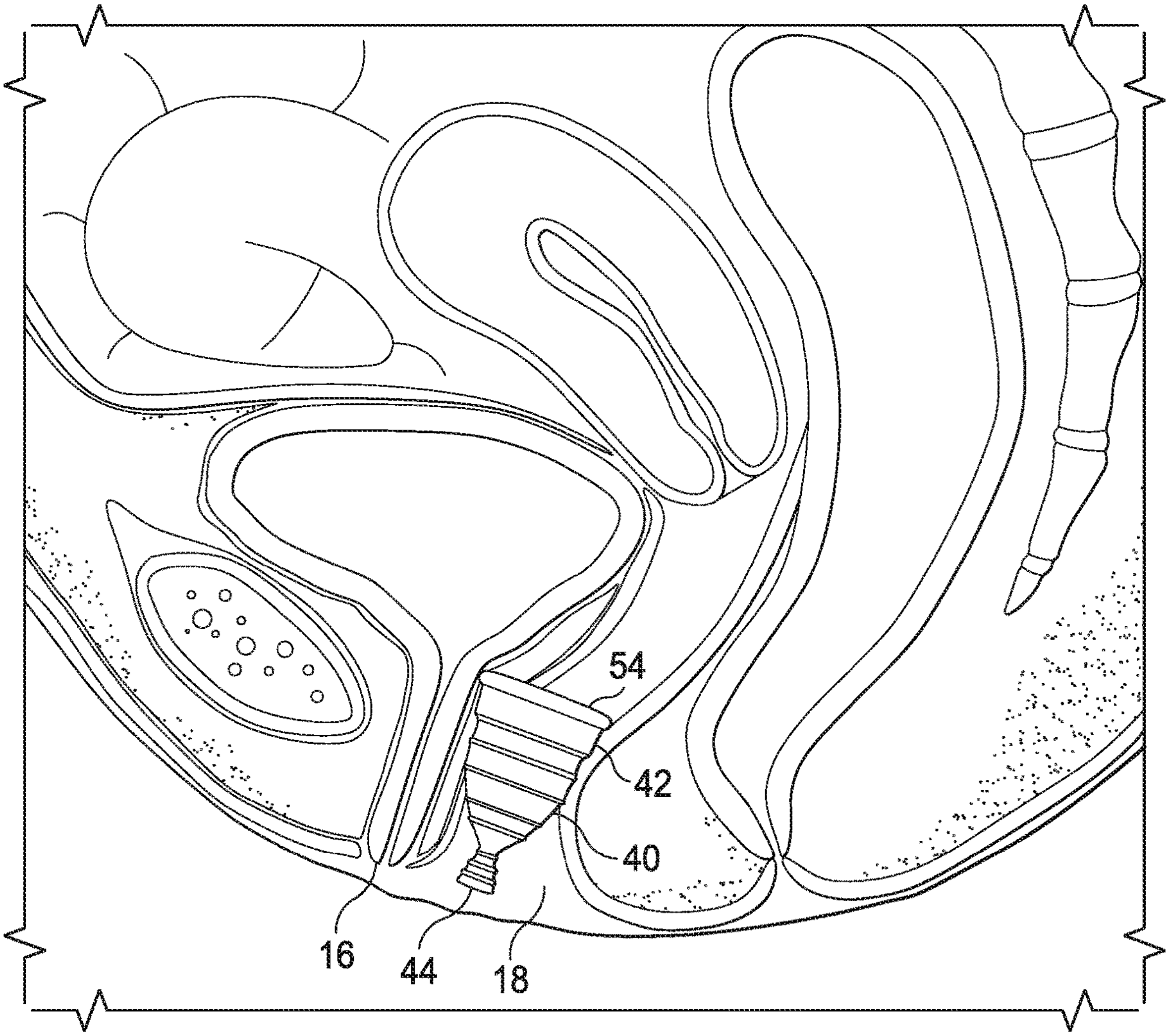
FIGS. 11-13 each illustrate a cross-section of the pelvic region of a female as well as an embodiment of the vaginal insert device inserted in the vagina.
Figure 12:
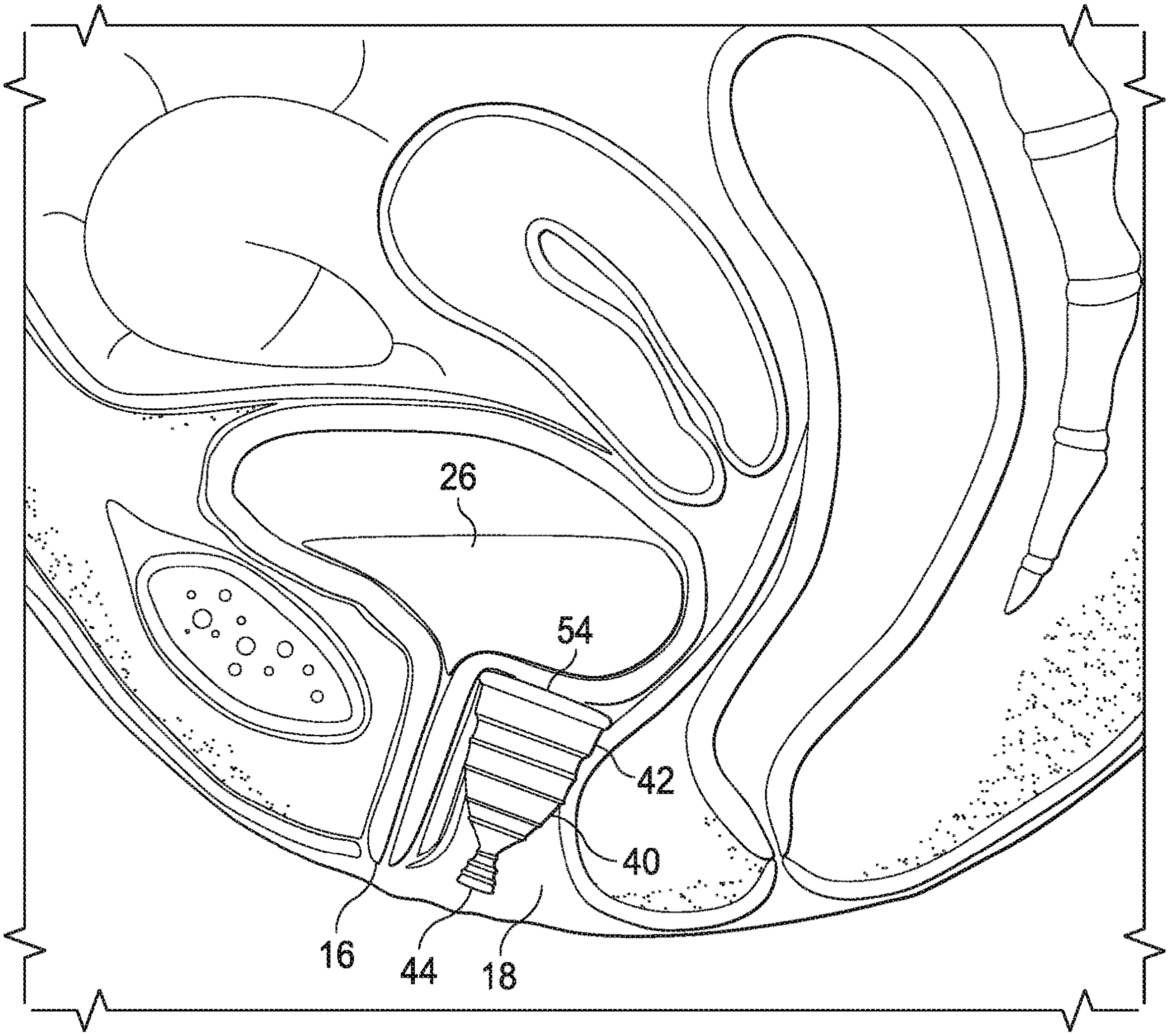
Figure 13:
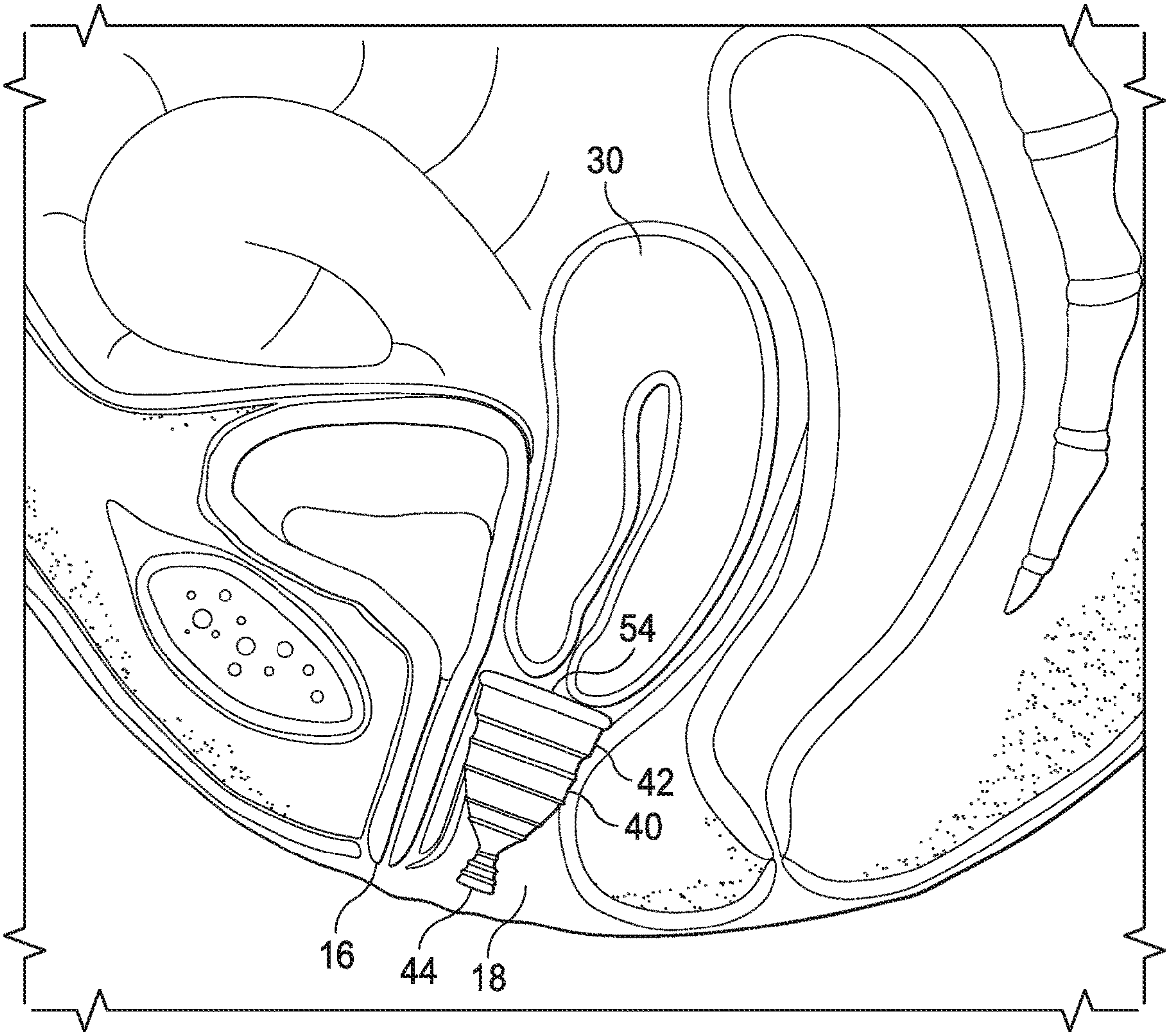

FIG. 11 is a cross-section of the pelvic region of a female illustrating an embodiment of the vaginal insert device 40 inserted in the vagina 18 and applying pressure on the urethral sphincter 16 to manage, improve, or eliminate female urinary incontinence. FIGS. 12 and 13 are each a cross-section of the pelvic region of a female illustrating an embodiment of the vaginal insert device 40 inserted in the vagina 18 to manage, improve, or eliminate POP, in addition to applying pressure on the urethral sphincter 16 to manage, improve, or eliminate female urinary incontinence. In particular, in FIG. 12, vaginal insert device 40 is inserted in the vagina 18 to manage, improve, or eliminate a prolapsed bladder 26. In particular, in FIG. 13, vaginal insert device 40 is inserted in the vagina 18 to manage, improve, or eliminate a prolapsed uterus 30. As illustrated in FIGS. 11-13, the upper open end 54 of the upper portion 42 is the innermost portion of the vaginal insert device 40 during insertion. As further illustrated in FIGS. 11-13, the removal portion or stem 44 of an embodiment of vaginal insert device 40 can be accessed from the exterior of the vagina 18 when the vaginal insert device is inserted and assists in removal of the vaginal insert device. Ridges 48 on stem 44 provide better grip for removal of the device 40 by a patient.

Figure 14A:
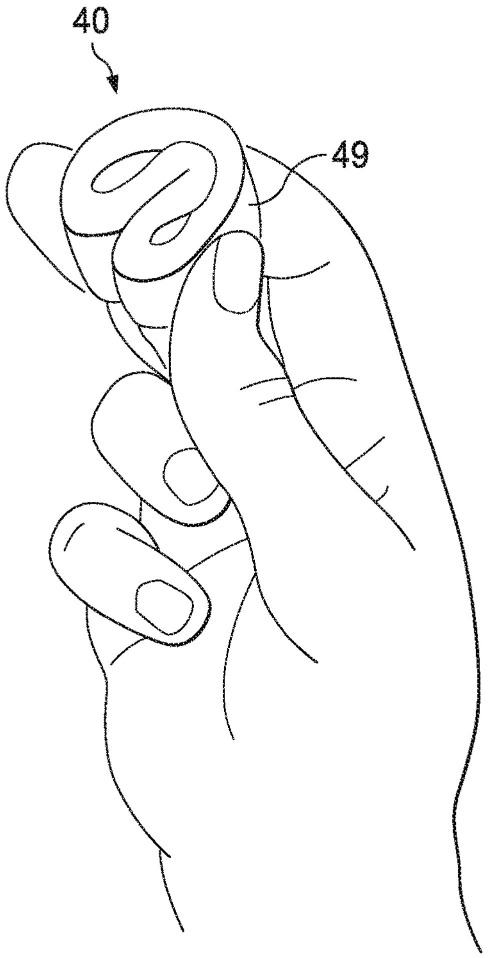
FIGS. 14A and 14B illustrate a method for inserting an embodiment of the vaginal insert device into a patient's vagina.
Figure 14B:
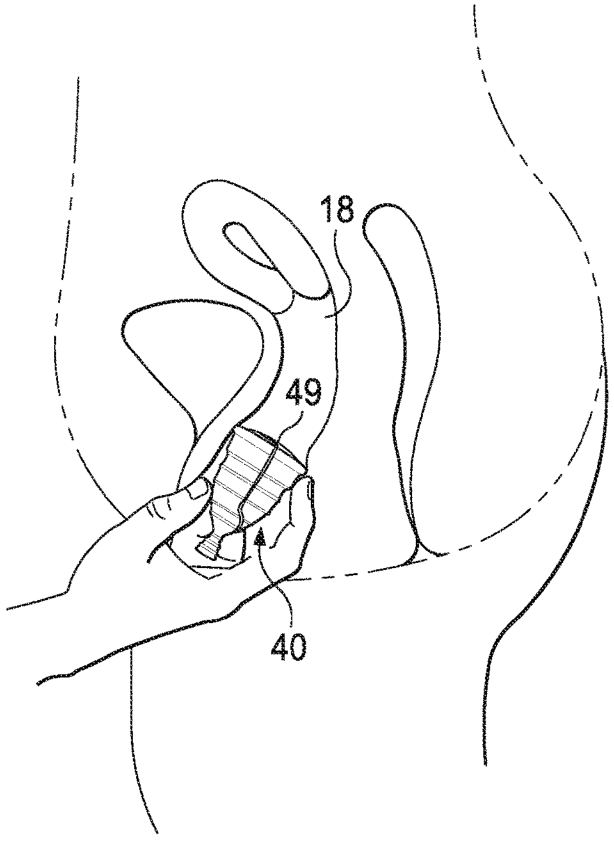

FIGS. 14A and 14B illustrate a method for comfortably inserting vaginal insert device 40 into vagina 18. As illustrated in FIG. 14A, a patient can manually squeeze the wall 49 of the upper portion to make the upper portion more compact for easier insertion of the vaginal insert device 40. As illustrated in FIG. 14B, once vaginal insert device 40 is manually inserted into vagina 18, wall 49 expands back to its original shape.

Figure 15C:
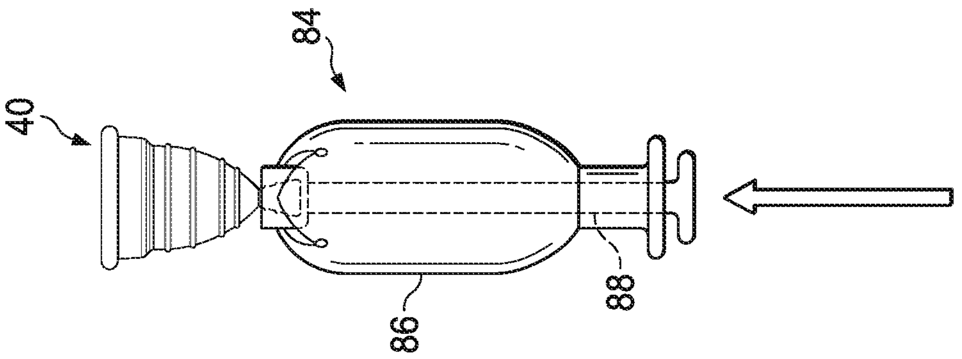
FIGS. 15B-15C illustrate a cross-section of the pessary applicator of FIG. 15A, and a method of using the same to insert an embodiment of the vaginal insert device into a patient's vagina.
Figure 15B:
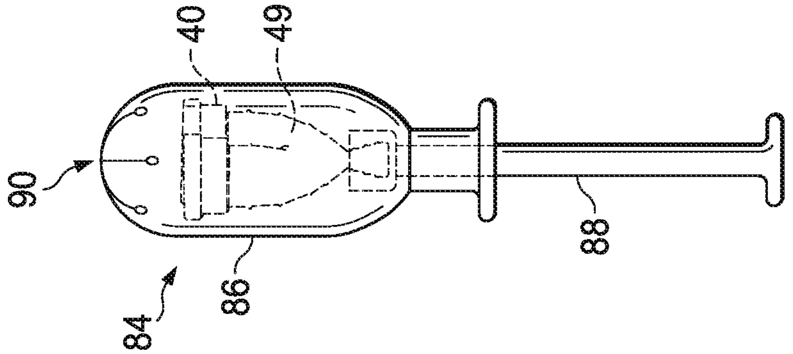
Figure 15A:
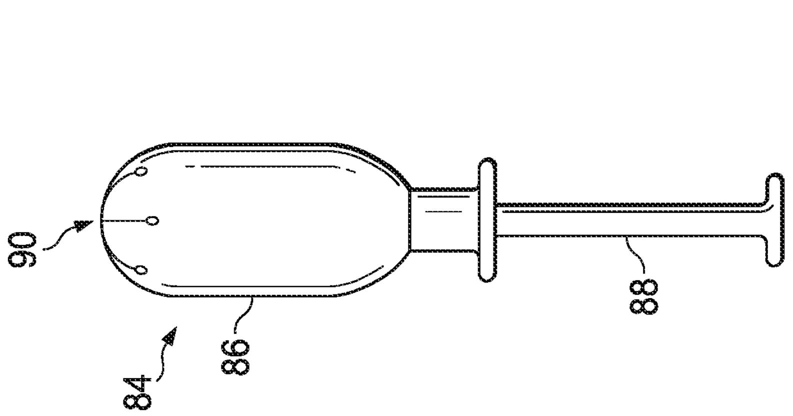
FIG. 15A illustrates a side-view of a pessary applicator.

FIG. 15A illustrates a side-view of a pessary applicator 84 which can be used to assist in inserting a vaginal insert device 40 into a patient's vagina 18. Pessary applicator 84 comprises an insertion member 86, a top portion 90 of the insertion member, and a plunger 88. Pessary applicator 84 is generally similar to a tampon applicator. However, the insertion member 86 will generally have a greater circumference than a tampon applicator to accommodate a vaginal insert device 40, which when compacted has a shape which is generally larger than the circumference of a tampon. FIGS. 15B-15C illustrate a cross-section of the pessary applicator 84 of FIG. 15A, and a method of using the applicator to comfortably insert a vaginal insert device 40 into a patient's vagina 18. As is illustrated, vagina insert device 40 is housed inside insertion member 86 in a compacted shape. Similar to the process of insertion of a tampon into a vagina using an applicator, insertion member 86 of applicator 84 is inserted into the patient's vagina 18, and the plunger 88 is pushed towards the insertion member, ejecting the vaginal insert device 40 through the top portion 90. The applicator 84 is then removed from the vagina 18, and the vaginal insert device 40 remains in place in the vagina, expanded back to its normal shape. The vaginal insert device 40 which has been inserted is positioned such as is illustrated in FIG. 11.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus, device or system or a component, section, or portion of an apparatus, device or system being adapted to, arranged to, capable of, configured to, enabled to, operable to, or operative to perform a particular function encompasses that apparatus, device, system, or component, whether or not it or that particular function is used, activated, turned on, or unlocked, as long as that apparatus, system, device or component is so adapted, arranged, capable, configured, enabled, operable, or operative.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

What is claimed is:

1. A method for managing, improving, or preventing pelvic organ prolapse, urinary incontinence, or both pelvic organ prolapse and urinary incontinence, the method comprising:

obtaining a vaginal insert device comprising a cone shaped body and a lower removal portion, the cone shaped body comprising an upper portion having an upper open end, a lower end having an opening, and an interior, the upper portion extending from the upper open end to the lower end, wherein the cone shaped body includes (i) a rim that surrounds and extends from an exterior surface of the cone shaped body at the upper open end of the upper portion, and (ii) a plurality of ridges that surrounds and extends from the exterior surface of the cone shaped body, with each ridge of the plurality of ridges being spaced apart from an adjacent ridge of the plurality of ridges between the rim and the lower end;

collapsing the cone shaped body of the vaginal insert device into a compact shape;

inserting the vaginal insert device, with the cone shaped body in the compact shape, into a vagina;

positioning the vaginal insert device adjacent a vaginal wall; and releasing the vaginal insert device to allow for the cone shaped body to shift from the compact shape and to attempt to return to an original shape;

wherein the vaginal insert device is configured to apply localized pressure to the urethral sphincter at the bladder neck and to directly support a pelvic organ to manage, improve, or prevent pelvic organ prolapse and urinary incontinence, while the vaginal insert device is in the vagina, wherein the rim and the plurality of ridges are configured to hold the vaginal insert device securely in place in the vagina and apply pressure to the pelvic organ or support the pelvic organ;

wherein the vaginal insert device is configured to equalize air pressure between the interior of the cone shaped body and an exterior of the cone shaped body, while the vaginal insert device is in the vagina; and wherein the opening of the lower end of the upper portion of the cone shaped body comprises a ventilation opening at a lower end apex for equalizing the air pressure.

2. The method of claim 1, wherein the pelvic organ is the bladder or the uterus.

3. The method of claim 1, wherein the vaginal insert device is further configured to manage involuntary leakage of urine during an activity, while the vaginal insert device is in the vagina.

4. The method of claim 3, wherein the activity is coughing, laughing, sneezing, lifting an object, or exercising.

5. The method of claim 1, further comprising leaving the vaginal insert device in the vagina for up to 12 hours.

6. The method of claim 1, further comprising removing the vaginal insert device by:

gripping the lower removal portion extending from the cone shaped body;

compressing the cone shaped body to the compact shape; and withdrawing the vaginal insert device from the vagina.

7. The method of claim 1, wherein the lower removal portion further comprises a plurality of ridges extending from an exterior side of the lower removal portion.

8. The method of claim 1, wherein at least one additional ventilation opening is provided in a portion of the cone shaped body.

9. The method of claim 1, wherein the cone shaped body has a circular transverse cross-section throughout its length.

10. The method of claim 1, wherein the lower removal portion further comprises a lower open end.

11. A method for managing, improving, or preventing pelvic organ prolapse, urinary incontinence, or both pelvic organ prolapse and urinary incontinence, the method comprising:

obtaining a vaginal insert device comprising a cone shaped body and a lower removal portion, the cone shaped body comprising an upper portion having an upper open end, a lower end having an opening, and an interior, the upper portion extending from the upper open end to the lower end, wherein the cone shaped body includes (i) a rim that surrounds and extends from an exterior surface of the cone shaped body at the upper open end of the upper portion, and (ii) a plurality of ridges that surrounds and extends from the exterior surface of the cone shaped body;

collapsing the cone shaped body of the vaginal insert device into a compact shape;

inserting the vaginal insert device, with the cone shaped body in the compact shape, into a vagina;

positioning the vaginal insert device adjacent a vaginal wall; and releasing the vaginal insert device to allow for the cone shaped body to shift from the compact shape and to attempt to return to an original shape;

wherein the vaginal insert device is configured to apply localized pressure to the urethral sphincter at the bladder neck and to directly support a pelvic organ to manage, improve, or prevent pelvic organ prolapse and urinary incontinence, while the vaginal insert device is in the vagina, wherein the rim and the plurality of ridges on the exterior surface of the vaginal insert device are configured to hold the vaginal insert device securely in place in the vagina and apply pressure to the pelvic organ or support the pelvic organ;

wherein the vaginal insert device is configured to equalize air pressure between the interior of the cone shaped body and an exterior of the cone shaped body, while the vaginal insert device is in the vagina; and wherein the opening of the lower end of the upper portion of the cone shaped body comprises a ventilation opening at a lower end apex for equalizing the air pressure.

12. The method of claim 11, wherein the lower removal portion further comprises a plurality of ridges extending from an exterior side of the lower removal portion.

13. The method of claim 11, wherein at least one additional ventilation opening is provided in a portion of the cone shaped body.

14. The method of claim 11, wherein the cone shaped body has a circular transverse cross-section throughout its length.

15. The method of claim 11, wherein the lower removal portion further comprises a lower open end.

16. The method of claim 11, further comprising removing the vaginal insert device by:

gripping the lower removal portion extending from the cone shaped body;

compressing the cone shaped body to the compact shape; and withdrawing the vaginal insert device from the vagina.

* * * * *